(12) United States Patent
Gao et al.

(10) Patent No.: US 9,505,704 B2
(45) Date of Patent: Nov. 29, 2016

(54) INTERMEDIATE FOR SYNTHESIZING TREPROSTINIL DIETHANOLAMINE AND METHOD FOR PREPARING THE SAME

(71) Applicant: Everlight Chemical Industrial Corporation, Taipei (TW)

(72) Inventors: Shijay Gao, Taoyuan County (TW); Chia-Chung Tsai, Taoyuan County (TW); Tsai-Yung Chou, Taoyuan County (TW); Yu-Min Chiang, Taoyuan County (TW); Chi-Hsiang Yao, Taoyuan County (TW)

(73) Assignee: EVERLIGHT CHEMICAL INDUSTRIAL CORPORATION, Taipei (TW)

( * ) Notice: Subject to any disclaimer, the term of this patent is extended or adjusted under 35 U.S.C. 154(b) by 0 days.

(21) Appl. No.: 14/934,217

(22) Filed: Nov. 6, 2015

(65) Prior Publication Data
US 2016/0152548 A1 Jun. 2, 2016

(30) Foreign Application Priority Data
Dec. 1, 2014 (TW) .............................. 103141569 A

(51) Int. Cl.

| | | |
|---|---|---|
| C07C 69/76 | (2006.01) |
| C07C 69/757 | (2006.01) |
| C07D 307/92 | (2006.01) |
| C07C 45/59 | (2006.01) |
| C07C 45/62 | (2006.01) |
| C07C 41/28 | (2006.01) |
| C07C 51/09 | (2006.01) |
| C07C 213/08 | (2006.01) |
| C12P 13/00 | (2006.01) |
| C07C 67/31 | (2006.01) |
| C07C 37/055 | (2006.01) |
| C07C 69/16 | (2006.01) |
| C12P 7/62 | (2006.01) |
| C07C 39/17 | (2006.01) |
| C07C 41/26 | (2006.01) |
| C07C 43/23 | (2006.01) |
| C07C 51/38 | (2006.01) |
| C07C 59/72 | (2006.01) |

(52) U.S. Cl.
CPC ........... *C07C 69/757* (2013.01); *C07C 37/055* (2013.01); *C07C 39/17* (2013.01); *C07C 41/26* (2013.01); *C07C 41/28* (2013.01); *C07C 43/23* (2013.01); *C07C 45/59* (2013.01); *C07C 45/62* (2013.01); *C07C 51/09* (2013.01); *C07C 51/38* (2013.01); *C07C 59/72* (2013.01); *C07C 67/31* (2013.01); *C07C 69/16* (2013.01); *C07C 213/08* (2013.01); *C07D 307/92* (2013.01); *C12P 7/62* (2013.01); *C12P 13/001* (2013.01); *C07C 2102/10* (2013.01); *C07C 2103/14* (2013.01)

(58) Field of Classification Search
CPC ... C07C 213/08; C07C 37/055; C07C 67/31; C07C 2102/10; C07C 2103/14; C07C 215/12; C07C 39/17; C07C 41/28; C07C 45/59; C07C 45/62; C07C 51/09; C07C 69/712; C07C 69/757; C07C 29/15; C07C 67/03; C07C 69/013; C07C 69/16; C07D 307/92; C12P 13/001; C12P 7/62
See application file for complete search history.

(56) References Cited

U.S. PATENT DOCUMENTS 4,668,814 A  5/1987 Aristoff

FOREIGN PATENT DOCUMENTS

| CN | 103709194 A | 4/2014 |
| CN | 104086374 A | 10/2014 |
| TW | 201425323 A | 7/2014 |
| WO | 2013024052 A1 | 2/2013 |
| WO | 2013174848 A2 | 11/2013 |
| WO | WO2014/110491 | * 7/2014 |

\* cited by examiner

*Primary Examiner* — Yevegeny Valenrod
*Assistant Examiner* — Blaine G Doletski
(74) *Attorney, Agent, or Firm* — Bacon & Thomas, PLLC

(57) ABSTRACT

The present invention relates to a method for treprostinil diethanolamine synthesis. The present invention also relates to a novel intermediate used in the method for treprostinil diethanolamine synthesis. The novel intermediate is shown in the following formula (II):

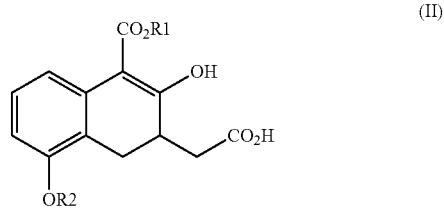

wherein R1 and R2 are described in the description.

12 Claims, 1 Drawing Sheet

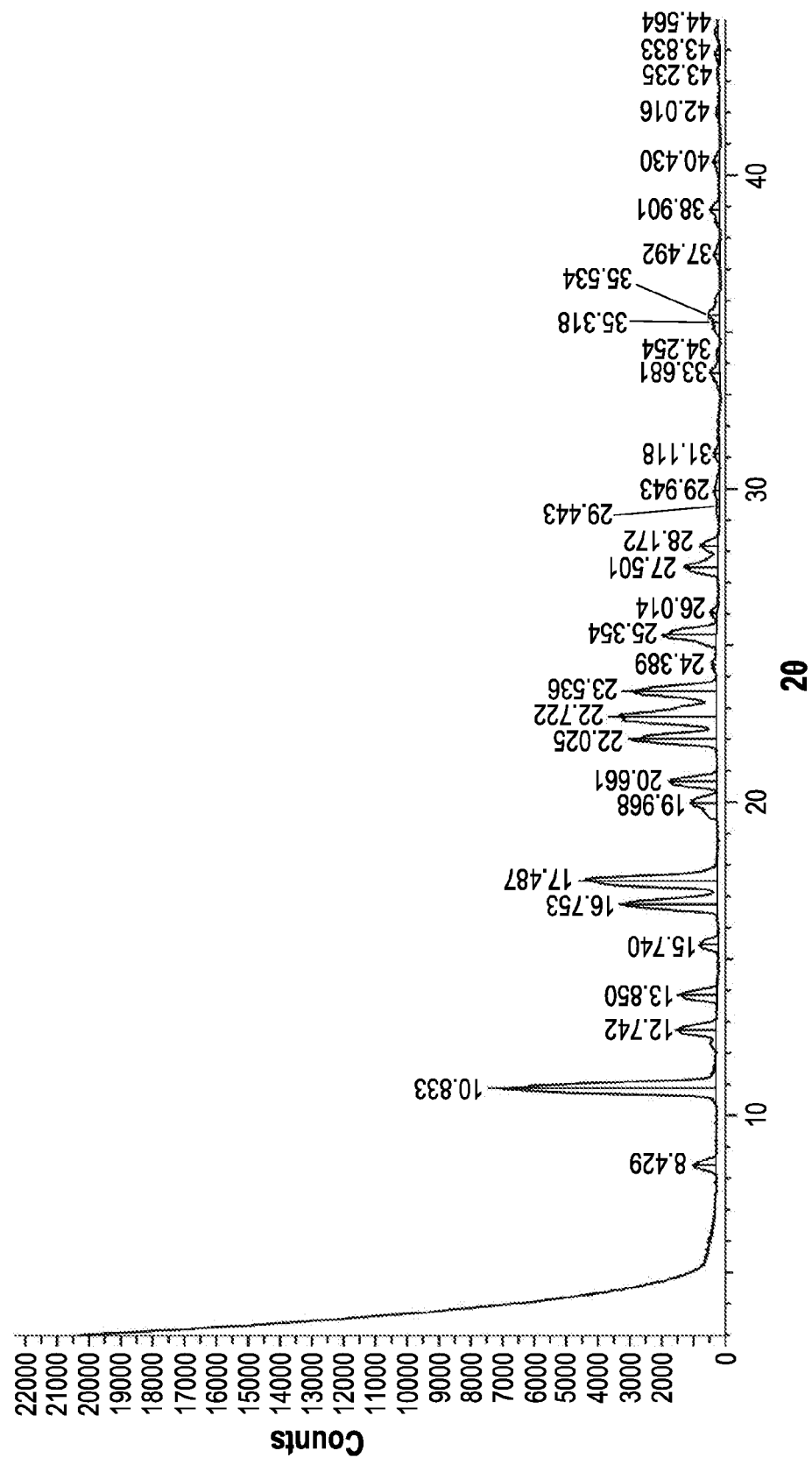

INTERMEDIATE FOR SYNTHESIZING TREPROSTINIL DIETHANOLAMINE AND METHOD FOR PREPARING THE SAME

CROSS REFERENCE TO RELATED APPLICATION

This application claims the benefits of the Taiwan Patent Application Serial Number 103141569, filed on Dec. 1, 2014, the subject matter of which is incorporated herein by reference.

BACKGROUND OF THE INVENTION

1. Field of the Invention

The present invention relates to a method for treprostinil diethanolamine preparation. In addition, the present invention also relates to a novel intermediate for treprostinil diethanolamine preparation.

2. Description of Related Art

Treprostinil and derivatives thereof are beneficial for vasodilation stimulation, platelet aggregation and thrombus formation inhibition, thrombolysis stimulation, cell proliferation inhibition, cytoprotection provision, atherosclerosis formation prevention, and angiogenesis induction. Accordingly, treprostinil may be applied to treat many kinds of diseases. However, to date, the existing methods for treprostinil synthesis are often complex and time consuming. In addition, the optical purity of the synthesized treprostinil also always needs to be considered for treprostinil synthesis.

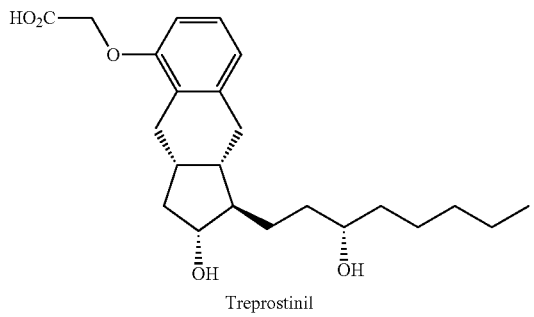 [SMILES: CCCCC[C@H](O)CC[C@@H]1[C@H]2Cc3cccc(OCC(=O)O)c3C[C@H]2C[C@H]1O]

Treprostinil

Therefore, there is a need to develop a novel method for treprostinil diethanolamine synthesis with less steps and to improve the optical purity of the synthesized treprostinil diethanolamine.

SUMMARY OF THE INVENTION

The object of the present invention is to provide a novel intermediate for treprostinil diethanolamine preparation. The intermediate is represented by the following formula (II):

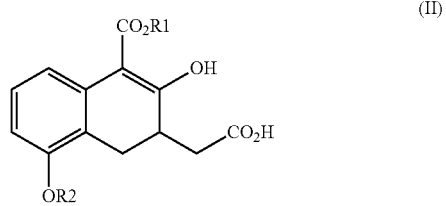

(II)

wherein each of R1 and R2 is a C1-6 alkyl group independently.

According to one embodiment of the present invention, in formula (II), R1 may be a methyl group.

According to one embodiment of the present invention, in formula (II), R2 may be a methyl group.

According to one embodiment of the present invention, the preparation method of the compound represented by formula (II) includes the following steps:

(i) providing 5-alkoxy-2-tetralone represented as below:

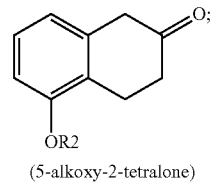

(5-alkoxy-2-tetralone)

wherein R2 may be a C1-6 alkyl group, and then performing an alkoxycarbonyl reaction using 5-alkoxy-2-tetralone to obtain a compound of formula (I) represented as below:

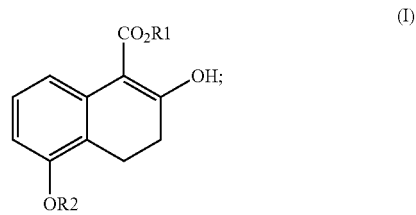

(I)

and (ii) performing an alkylation reaction using the compound of formula (I) to obtain a compound of formula (II).

The novel intermediate represented by formula (II) of the present invention is the intermediate generated during the preparation of the compound of formula (IV).

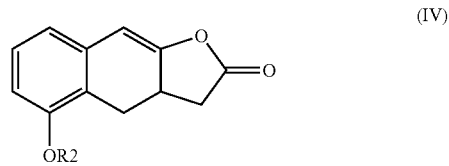

(IV)

Hence, the other object of the present invention is to provide a method for the preparation of a compound of formula (IV):

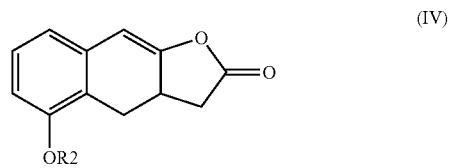

(IV)

wherein the method comprises the following steps:

(1) transforming a compound of formula (II) to obtain the compound of formula (IV);

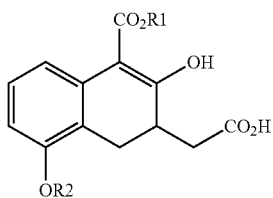

(II)

wherein each of R1 and R2 is a C1-6 alkyl group independently.

According to a preferred embodiment of the present invention, the step (1) described above may comprise the following steps:

(1-1) performing a decarbomethoxylation reaction using the compound of formula (II) to obtain a compound of formula (III); and

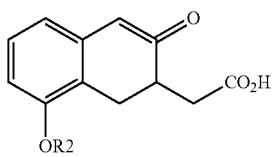

(III)

(1-2) performing a lactonization reaction using the compound of formula (III) to obtain a compound of formula (IV); wherein R2 is a C1-6 alkyl group and is preferred to be a methyl group.

The compound of formula (IV) prepared by using the novel intermediate described above may be used in the method for treprostinil preparation that will be described below.

Another object of the present invention is to provide a method for the preparation of treprostinil diethanolamine represented by formula (XII), wherein the method comprises the following steps (A) to (J).

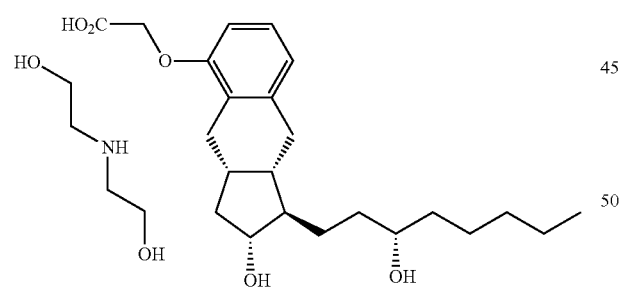

(XII)

The preparation method may comprise the following steps:

(A) reacting a compound of formula (IV)

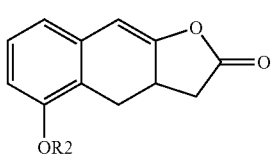

(IV)

with

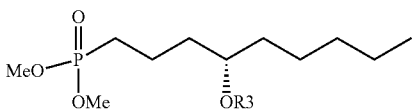

to perform a cyclization reaction to obtain a compound of formula (V):

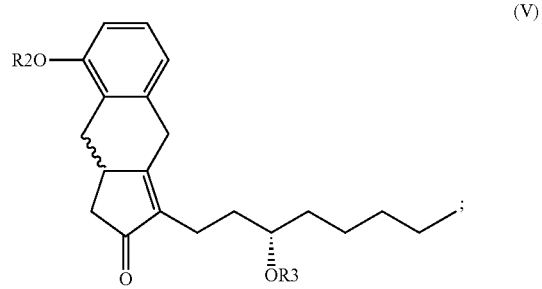

(V)

wherein R2 is a C1-6 alkyl group and R3 is a hydroxyl-protecting group;

(B) hydrogenating the compound of formula (V) to obtain a compound of formula (VI):

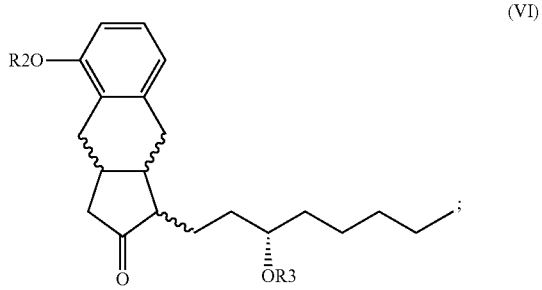

(VI)

(C) reducing the compound of formula (VI) to obtain a compound of formula (VII):

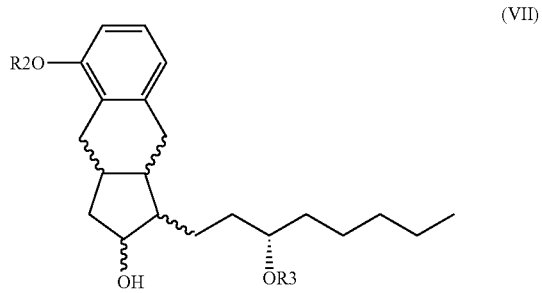

(VII)

(D) deprotecting the compound of formula (VII) to obtain a compound of formula (VIII):

(VIII)

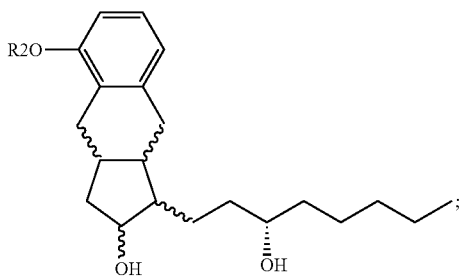

(E) performing a stereo-selective acetylation reaction using the compound of formula (VIII) in the presence of a lipase to obtain a compound of formula (VIII-1):

(VIII-1)

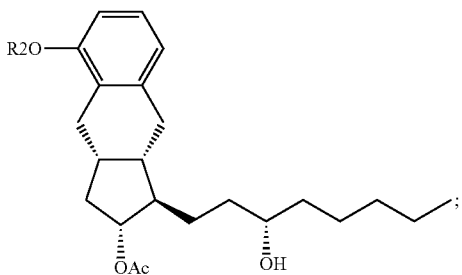

(F) performing a deacetylation reaction using the compound of formula (VIII-1) to obtain a compound of formula (VIII'):

(VIII')

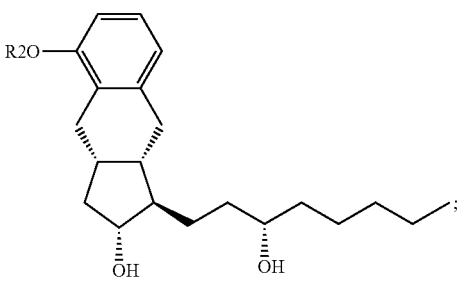

(G) performing a dealkylation reaction using the compound of formula (VIII') to obtain a compound of formula (IX):

(IX)

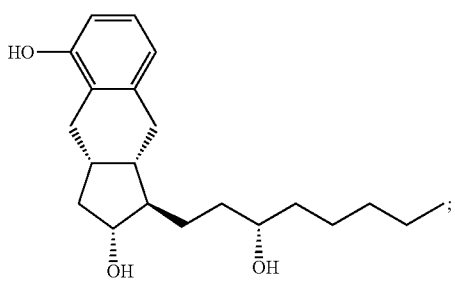

(H) performing an alkylation reaction using the compound of formula (IX) by reacting with

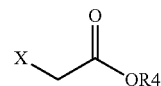

to obtain a compound of formula (X):

(X)

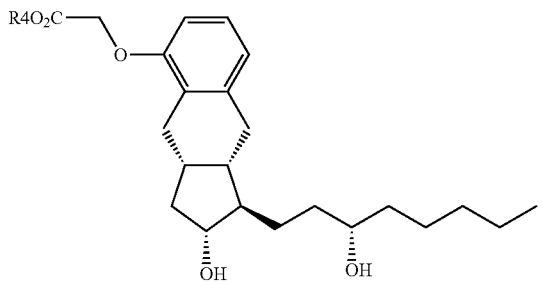

wherein R4 is a C1-5 alkyl group;

(I) hydrolyzing the compound of formula (X) to obtain a treprostinil represented by formula (XI):

(XI)

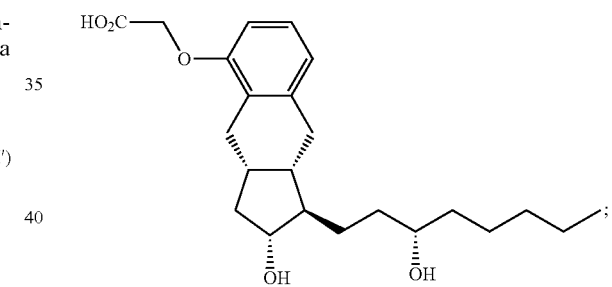

and (J) performing a salt formation reaction using the compound of formula (XI) with diethanolamine to obtain a treprostinil diethanolamine represented by formula (XII).

In a preferred embodiment of the present invention, R2 and R4 are methyl groups independently.

In step (A) of another embodiment of the present invention, the hydroxyl-protecting group (R3) may be a protecting group known in the art and is not particularly limited. However, the hydroxyl-protecting group is preferably selected from the group consisting of methyl group, ethyl group, tert-butyl group, acetyl group, pivaloyl group (Piv), benzyl group (Bn), p-methoxy benzyl group (PMB), 9-fluorenylmethyl group (Fm), diphenylmethyl group (DPM), trimethylsilyl group (TMS), tert-butyldimethylsilyl group (TBS), triisopropylsilyl group (TIPS), 2-methoxylethoxymethyl group (MEM), methylthiomethy group (MTM), methoxymethyl group (MOM), and tetrahydropyranyl group (THP). Based on the species used as the hydroxyl-protecting group in step (A), different deprotecting agents should be used accordingly in the deprotecting reaction in step (D). For example, when tetrahydropyran (THP) is used as the hydroxyl-protecting group, the deprotecting reaction thereof may be performed by using the p-Toluenesulfonic acid dissolved in methanol to deprotect the protecting group.

After a stereo-selective acetylation reaction is performed using the compound of formula (VIII) in the presence of a lipase in step (E), a compound of formula (VIII') is collected after the separation and the deprotecting reaction. The collected compound is then re-crystallized to increase the purity of the intermediate. The suitable solvent used for this re-crystallization is known in the art, and may be selected by a person skilled in the art without particular limitation. For example, the solvent used for recrystallization herein may be a chlorinated solvent, such as dichloromethane, chloroform, carbon tetrachloride, or the like; alcohols, such as methanol, ethanol, isopropanol, n-propanol, or the like; ketones, such as acetone, methyl ethyl ketone, methyl isobutyl ketone, acetophenone, or the like; esters, such as ethyl acetate, methyl acetate, isopropyl acetate, or tert-butyl acetate; ethers, such as tetrahydrofuran, diethyl ether, or methyl tertiary butyl ether; or may be acetonitrile, C5-8 alkane, or the like.

In one embodiment of the present invention, R4 in step (H) is a methyl group.

Another object of the present invention is to provide another novel intermediate for treprostinil diethanolamine preparation. The intermediate is a compound of formula (VIII-1):

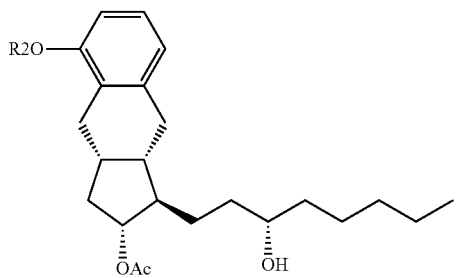

(VIII-1)

wherein R2 is a C1-6 alkyl group, and in a preferred embodiment of the present invention, R2 is a methyl group.

In every reaction steps disclosed by the present invention, the reacting agents, reacting conditions and parameters thereof are all general knowledge known by the person skilled in the art. The following example is a detailed description of an embodiment of the present invention, which may be altered or modified by a person skilled in the art without limitations.

The method for treprostinil diethanolamine synthesis provided by the present invention may efficiently improve the tedious and lengthy synthetic process currently existed for treprostinil diethanolamine synthesis. Furthermore, in the synthetic process of the present invention, by performing a stereo-selective acetylation to increase the purity of the intermediate, a treprostinil diethanolamine with high optical purity can be provided.

BRIEF DESCRIPTION OF THE DRAWINGS

FIG. 1 is a XRD spectrum analysis of compound 9 prepared by Example 11.

DETAILED DESCRIPTION OF THE PREFERRED EMBODIMENT

The following examples 1-4 show the detailed preparation method for a compound of formula (IV). The preparation method is as the following Reaction Scheme 1. In this example, R2 is a methyl group.

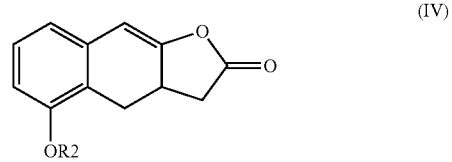

(IV)

The following Reaction Scheme 1, however, is only an embodiment of the present invention. The reagents and the reaction parameters of each reaction step in Reaction Scheme 1 may be altered or modified by those skilled in the art as long as the same product of each reaction step can be obtained.

Reaction Scheme 1:

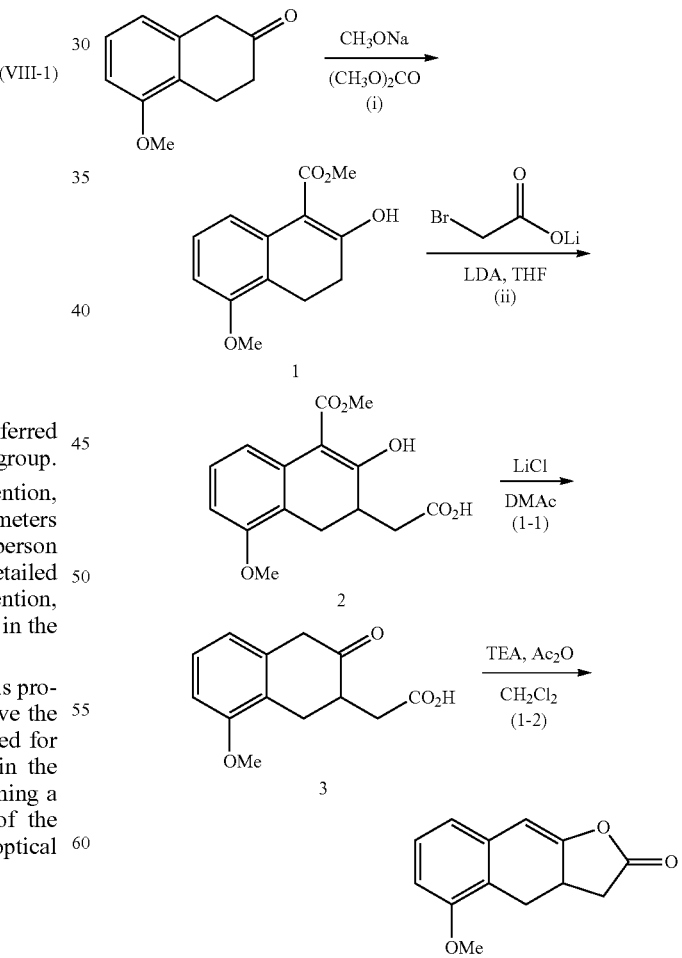

Example 1

Preparation of Compound 1 —Methoxycarbonyl Reaction (i)

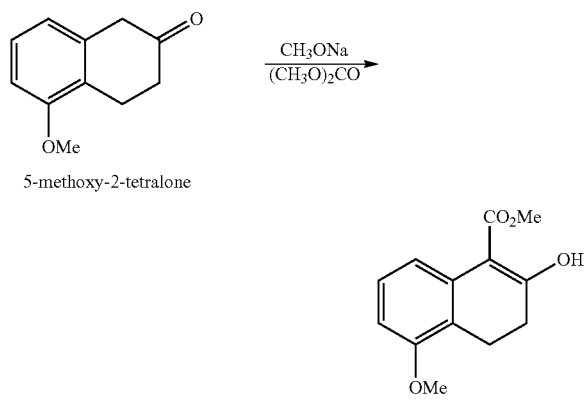

5-methoxy-2-tetralone

An amount of 500 g of 5-methoxy-2-tetralone was dissolved in 3.75 L of dimethyl carbonate. At 15° C., 633 mL of 30% methanolic sodium methoxide solution was then added. The reaction solution was next heated at 70° C. for 1 h. After the reaction solution was cooled to room temperature, the reaction was quenched by 1.2 L of 3N aqueous hydrochloric acid. The organic layer was separated and the aqueous layer was extracted using 1 L of ethyl acetate. The combined organic layers were concentrated in vacuum. The resulting crude product was extracted using 3.29 L of hexane and filtered. The filtrate was concentrated and dried to yield 531 g of compound 1 as yellow solid.

Example 2

Preparation of Compound 2 —Alkylation Reaction (ii)

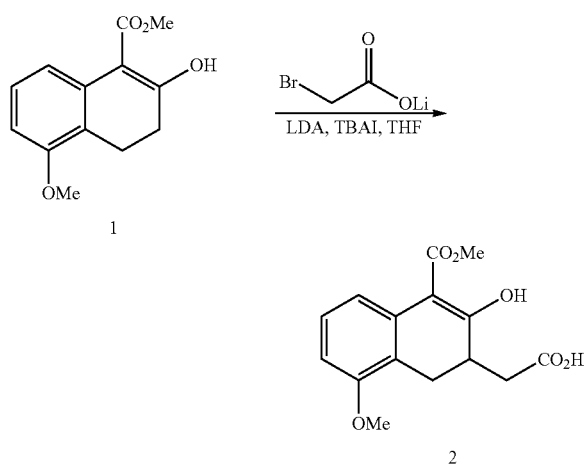

A solution of 143 mL of diisopropylamine was dissolved in 1 L of THF. At −60° C., 272 mL of 1.6 M n-butyl lithium in n-hexane was added dropwise and stirred for 15 min at −60° C. 92 g of compound 1 dissolved in 600 mL of THF was then added dropwise and stirred for 1 h at −60° C. Next, at 5° C., 68 g of lithium bromoacetate

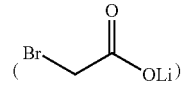

and 29 g of tetrabutylammonium iodide (TBAI) were then added. The reaction solution was stirred for 22 h at room temperature. The reaction was then quenched by 1.5 L of 2N aqueous hydrochloric acid at 5° C. After the organic layer was separated, the organic layer was washed twice using 1.5 L of 2N aqueous hydrochloric acid. The organic layer was then concentrated in vacuum to yield 110 g of compound 2 as off-white solid. In particular, this compound 2 is a preferred embodiment of the novel intermediate of the present invention. $^1$H NMR (CDCl$_3$, 400 MHz) δ 7.33-7.31 (d, J=8.0 Hz, 1H), 7.18-7.14 (t, J=8.0 Hz, 1H), 6.73-6.71 (d, J=8.0 Hz, 1H), 3.91 (s, 3H), 3.82 (s, 3H), 3.10-3.07 (m, 2H), 2.79-2.75 (m, 1H), 2.75-2.70 (m, 1H), 2.47-2.41 (m, 1H); $^{13}$C NMR (CDCl$_3$, 100 MHz) δ 178.9, 176.7, 173.3, 156.8, 132.7, 127.5, 120.4, 119.4, 108.7, 100.5, 56.3, 52.6, 36.0, 34.5, 25.8.

Example 3

Preparation of Compound 3—Decarbomethoxylation Reaction (1-1)

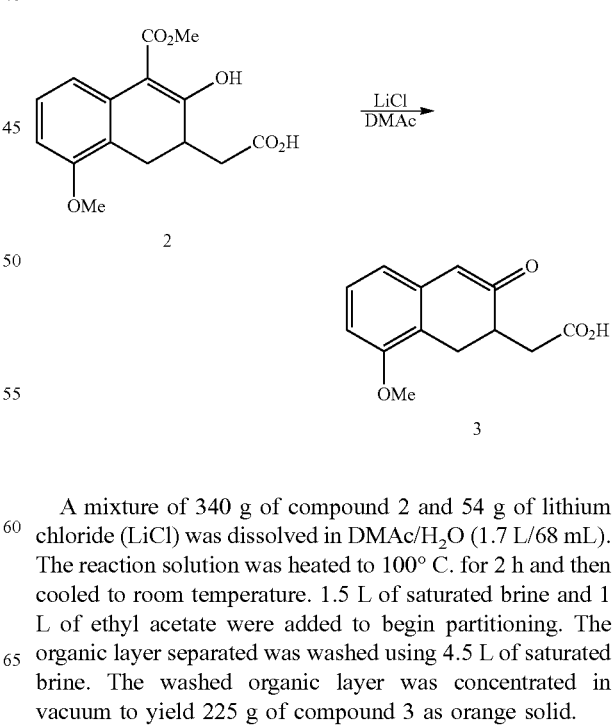

A mixture of 340 g of compound 2 and 54 g of lithium chloride (LiCl) was dissolved in DMAc/H$_2$O (1.7 L/68 mL). The reaction solution was heated to 100° C. for 2 h and then cooled to room temperature. 1.5 L of saturated brine and 1 L of ethyl acetate were added to begin partitioning. The organic layer separated was washed using 4.5 L of saturated brine. The washed organic layer was concentrated in vacuum to yield 225 g of compound 3 as orange solid.

Example 4

Preparation of Compound 4 —Lactonization Reaction (1-2)

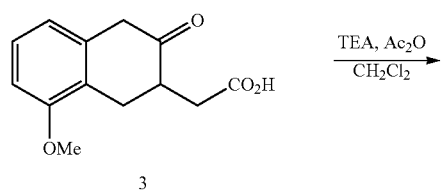

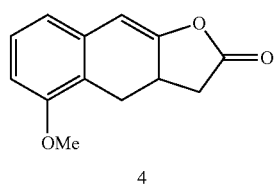

An amount of 225 g of compound 3 was dissolved in 2.25 L of dichloromethane (CH$_2$Cl$_2$, DCM). At 5° C., 335 mL of triethylamine (TEA) and 90 mL of acetic anhydride (Ac$_2$O) were then added. The reaction solution was stirred at room temperature for 1 h. 2 L of saturated brine was added to begin partitioning. The organic layer separated was washed using 1 L of 2N aqueous hydrochloric acid and concentrated in vacuum to yield a residue. The residue was purified using a silica gel column and was quickly eluted by using dichloromethane and hexane (1:1) as the elution buffer. The solid obtained after the solvent had been removed was recrystallized using ethyl acetate and hexane (1 L/2 L) to yield 173 g of compound 4 as white solid. $^1$H NMR (CDCl$_3$, 400 MHz) δ 7.19~7.15 (m, 1H), 6.76-6.73 (m, 2H), 6.10 (d, J=5.6 Hz, 1H), 3.84 (s, 3H), 3.61 (dd, J=7.2 Hz, 5.6 Hz, 1H), 3.23-3.11 (m, 1H), 2.95 (dd, J=17.6 Hz, 9.6 Hz, 1H), 2.49 (dd, J=17.6 Hz, 10.4 Hz, 1H), 2.36 (t, J=15.6 Hz, 1H), 1.58 (s, 2H); $^{13}$C NMR (CDCl$_3$, 100 MHz) δ 174.1, 156.2, 154.8, 134.9, 127.7, 119.5, 119.4, 109.0, 101.1, 55.4, 34.7, 33.1, 27.2

The following examples 5-14 show the detailed preparation method for compound 12 (as represented by formula (XII)). The preparation method is as the following Reaction Scheme 2.

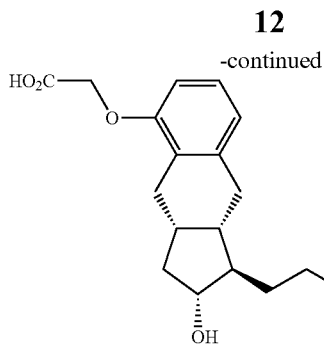

The following Reaction Scheme 2, however, is only an embodiment of the present invention. The reagents and the reaction parameters of each reaction step in Reaction Scheme 2 may be altered and modified by those skilled in the art as long as the same product of each reaction step can be obtained.

Reaction Scheme 2:

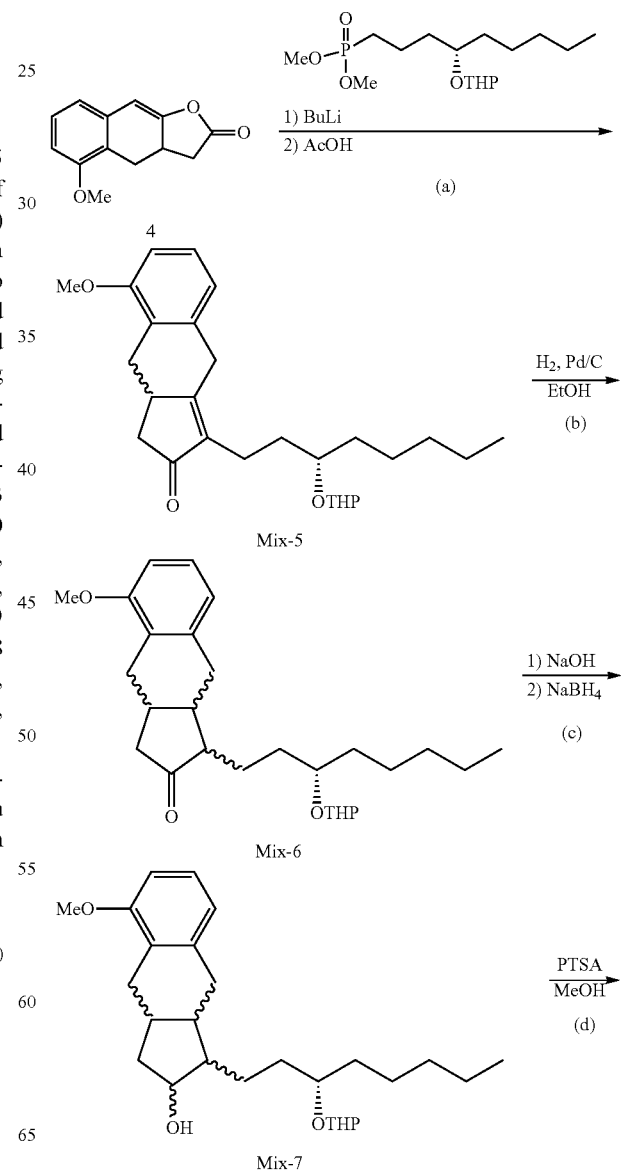

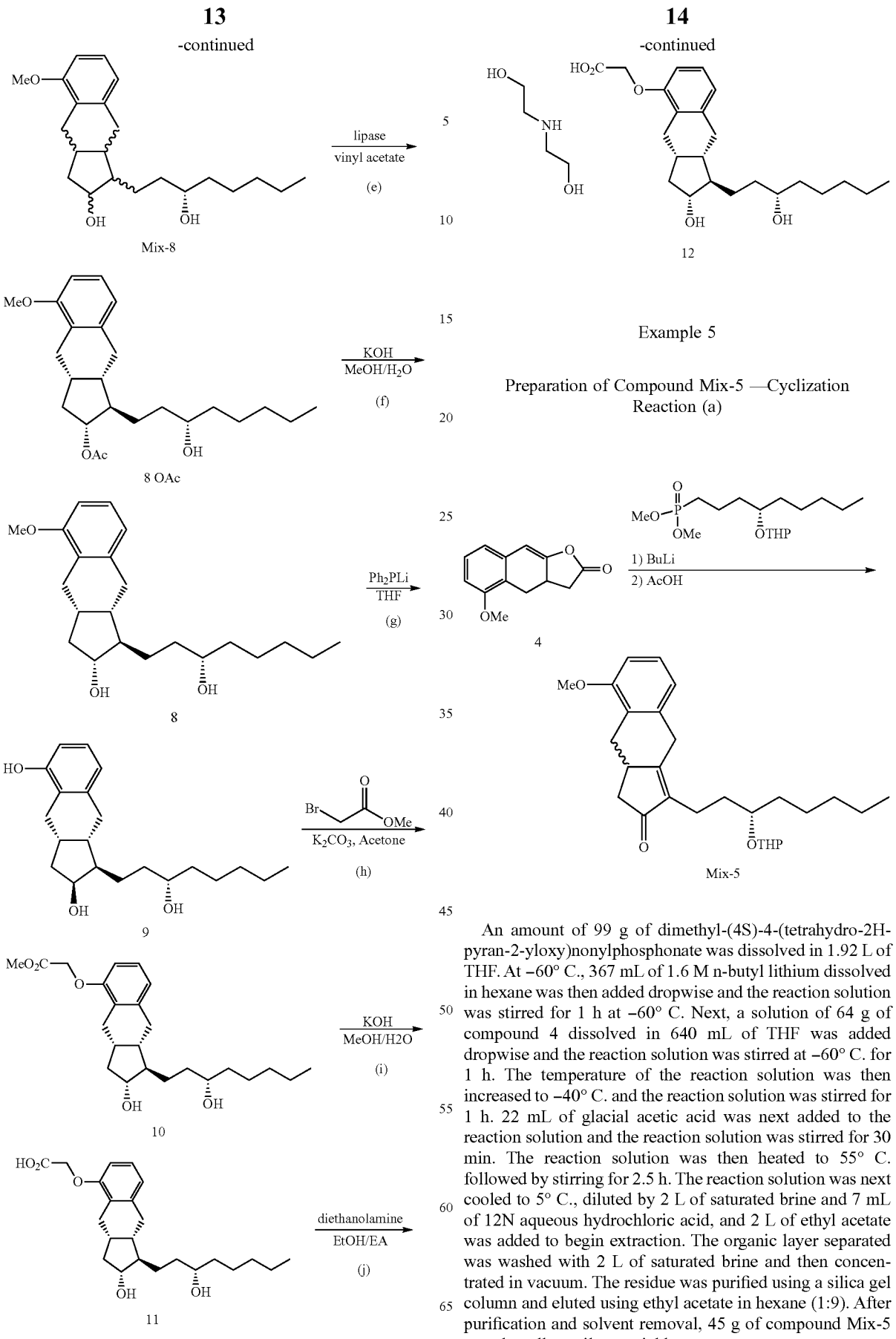

Example 5

Preparation of Compound Mix-5 —Cyclization Reaction (a)

An amount of 99 g of dimethyl-(4S)-4-(tetrahydro-2H-pyran-2-yloxy)nonylphosphonate was dissolved in 1.92 L of THF. At −60° C., 367 mL of 1.6 M n-butyl lithium dissolved in hexane was then added dropwise and the reaction solution was stirred for 1 h at −60° C. Next, a solution of 64 g of compound 4 dissolved in 640 mL of THF was added dropwise and the reaction solution was stirred at −60° C. for 1 h. The temperature of the reaction solution was then increased to −40° C. and the reaction solution was stirred for 1 h. 22 mL of glacial acetic acid was next added to the reaction solution and the reaction solution was stirred for 30 min. The reaction solution was then heated to 55° C. followed by stirring for 2.5 h. The reaction solution was next cooled to 5° C., diluted by 2 L of saturated brine and 7 mL of 12N aqueous hydrochloric acid, and 2 L of ethyl acetate was added to begin extraction. The organic layer separated was washed with 2 L of saturated brine and then concentrated in vacuum. The residue was purified using a silica gel column and eluted using ethyl acetate in hexane (1:9). After purification and solvent removal, 45 g of compound Mix-5 as pale yellow oil was yield.

Example 6

Preparation of Compound Mix-6 —Hydrogenation (b)

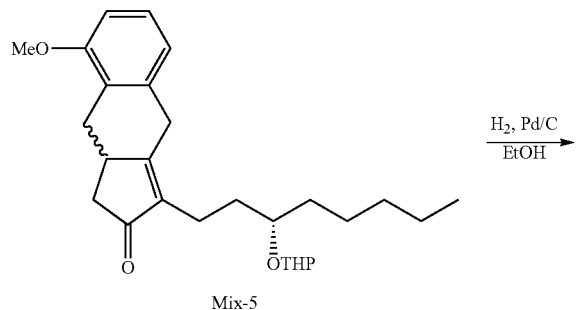

Mix-5

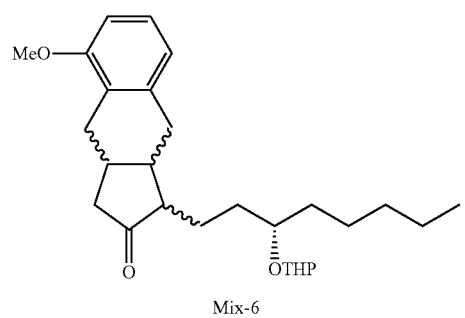

Mix-6

A mixture of 45 g of compound Mix-5, 1.0 g of potassium carbonate, and 5.6 g of 10% palladium on carbon (Pd/C) was dissolved in 360 mL of ethanol. The reaction mixture was hydrogenated at 50 psi of pressure at room temperature for 7 h. The reaction mixture was filtered using Celite and the filtrate was concentrated in vacuum. The filtrate was purified using a silica gel column and eluted using ethyl acetate and hexane (1:19). After purification and solvent removal, 40 g of compound Mix-6 as colorless oil was yield.

Example 7

Preparation of Compound Mix-7 —Reduction (c)

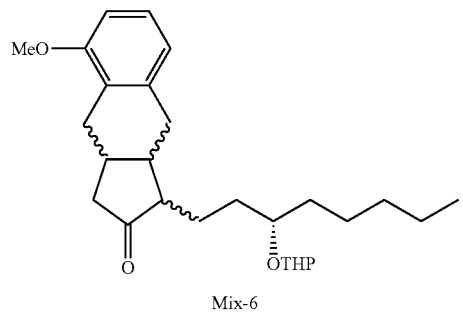

Mix-6

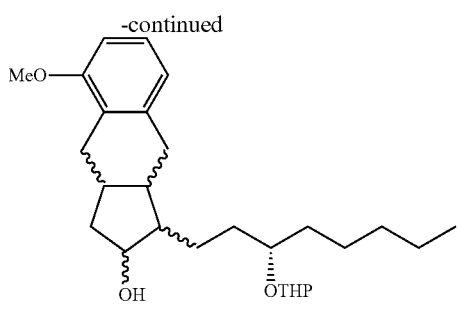

Mix-7

An amount of 30 g of compound Mix-6 was dissolved in 600 mL of ethanol. At −10° C., aqueous sodium hydroxide solution (28 g of sodium hydroxide dissolved in 140 mL of water) was added dropwise and the reaction solution was stirred for 30 min. Next, at −10° C., 2.7 g of $NaBH_4$ was added and the reaction solution was stirred for 1 h. An additional 2.7 g of $NaBH_4$ was then added and the reaction solution was stirred for another 2 h. The reaction was next quenched by adding glacial acetic acid. The solvent was removed under reduced pressure. The residue was dissolved in 52 mL of ethyl acetate, washed with aqueous $NaHCO_3$ and saturated brine, and concentrated in vacuum to yield 31 g of compound Mix-7 as colorless oil.

Example 8

Preparation of Compound Mix-8 —Deprotecting Reaction (d)

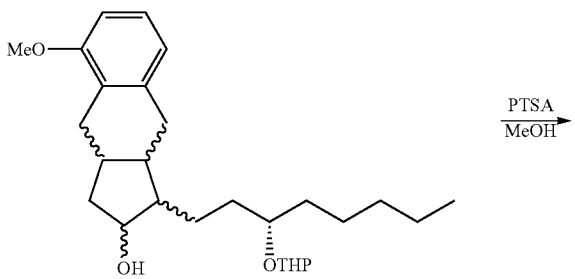

Mix-7

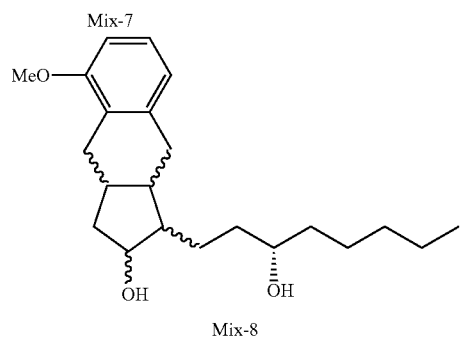

Mix-8

A mixture of 64 g of compound Mix-7 and 1.3 g of p-Toluenesulfonic acid (PTSA) was dissolved in 640 mL of methanol. The reaction solution was stirred at room temperature for 2 h. The reaction solution was concentrated in vacuum and purified using a silica gel column with ethyl acetate and hexanes (3:7) as the elution buffer. After purification and solvent removal, 40 g of compound Mix-8 as colorless oil was yield.

Example 9

Preparation of Compound 8 OAc —Acetylation Reaction (e)

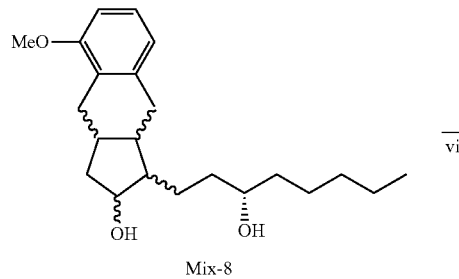

Mix-8

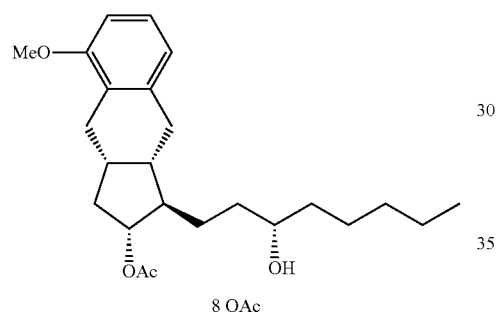

8 OAc

A mixture of 38 g of compound Mix-8 and 17 g of Lipase AK (AMANO) was dissolved in 750 mL of hexane and 146 mL of vinyl acetate. The reaction solution was stirred at room temperature for 22 h. The reaction solution was filtered and concentrated in vacuum. The filtrate was purified using a silica gel column with ethyl acetate and hexanes (1:7) as the elution buffer. After purification and solvent removal, 19 g of compound 8 OAc as colorless oil was yield. $^1$H NMR (CDCl$_3$, 400 MHz) δ 7.11 (t, J=7.8 Hz, 1H), 6.77 (d, J=7.3 Hz, 1H), 6.75 (d, J=8.1 Hz, 1H), 4.78-4.72 (m, 1H), 3.81 (s, 3H), 3.62-3.54 (m, 1H), 2.81 (dd, J=15.0, 5.7 Hz, 1H), 2.78 (dd, J=15.4, 6.3 Hz, 1H), 2.50 (dd, J=12.0, 6.3 Hz, 1H), 2.47 (dd, J=12.7, 6.1 Hz, 1H), 2.35-2.25 (m, 2H), 1.98 (s, 3H), 1.98-1.89 (m, 1H), 1.63-1.52 (m, 3H), 1.52-1.25 (m, 10H), 1.23-1.12 (m, 1H), 0.89 (t, J=6.9 Hz, 3H); $^{13}$C NMR (CDCl$_3$, 100 MHz) δ 171.2, 156.7, 140.2, 126.4, 120.7, 126.8, 108.5, 79.1, 72.3, 55.7, 49.2, 40.7, 37.9, 37.6, 33.7, 35.1, 33.6, 32.1, 28.5, 25.8, 25.5, 22.8, 21.5, 14.3.

The reaction described above is a stereo-selective acetylation reaction. The hydroxyl group of the compound Mix-8 with specific stereo structure is protected by the acetylation (OAc) reaction in the presence of lipase. By purification using a silica gel column, the intermediate compound 8 OAc with high optical purity can be obtained.

Example 10

Preparation of Compound 8 —Deacetylation Reaction (f)

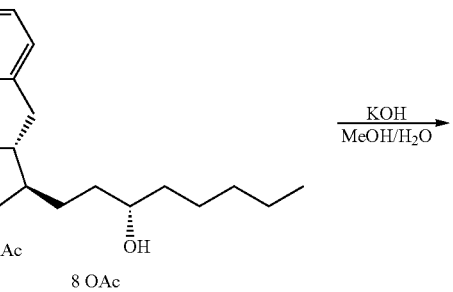

8 OAc

8

A mixture of 15 g of compound 8 OAc and 4.4 g of potassium hydroxide (KOH) was dissolved in 225 mL of methanol and 75 mL of water (MeOH/H$_2$O). The reaction solution was heated to reflux for 5 h. The methanol was removed from the reaction solution under reduced pressure. The aqueous layer was extracted using ethyl acetate. The organic layer was concentrated in vacuum to yield 10 g of compound 8 as colorless oil.

Example 11

Preparation of Compound 9 —Demethylation Reaction (2)

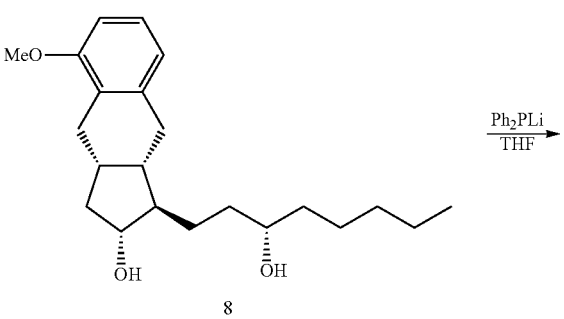

8

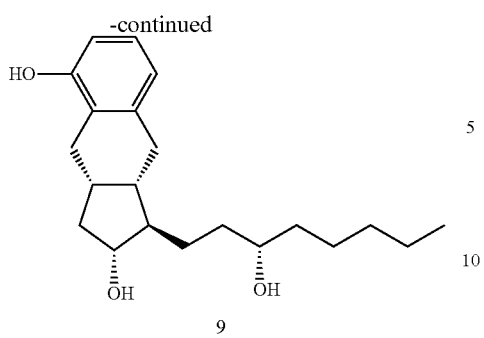

9

An amount of 37 g of diphenylphosphine was dissolved in 245 mL of THF. At 5° C., 150 mL of 1.6 M n-butyl lithium (in hexane) was added dropwise and the reaction solution was stirred for 1 h. Next, at 5° C., 3/7 portion of the lithium diphenylphospine solution described above was added to another flask containing a solution of 11.0 g of compound 8 in 49 mL of THF. The reaction solution was then heated and refluxed for 2 h. After the reaction solution was cooled to room temperature, the remaining 4/7 portion of the lithium diphenylphosphine solution described above was added. The reaction solution was again heated and refluxed for 17 h. After the reaction solution was cooled to 5° C., the reaction was quenched using aqueous HCl. The organic layer was separated and the aqueous layer was extracted using dichloromethane. The combined organic layers were concentrated in vacuum. The crude product was purified using a silica gel column with methanol in dichloromethane (1:19) as the elution buffer. After purification and solvent removal, the crude product was then recrystallized using ethyl acetate and dichloromethane to yield 8.3 g of compound 9 as white solid. The compound 9 prepared by the present example has a crystalline structure and the XRD analysis spectrum thereof is shown in FIG. 1.

Example 12

Preparation of Compound 10 — Alkylation Reaction (h)

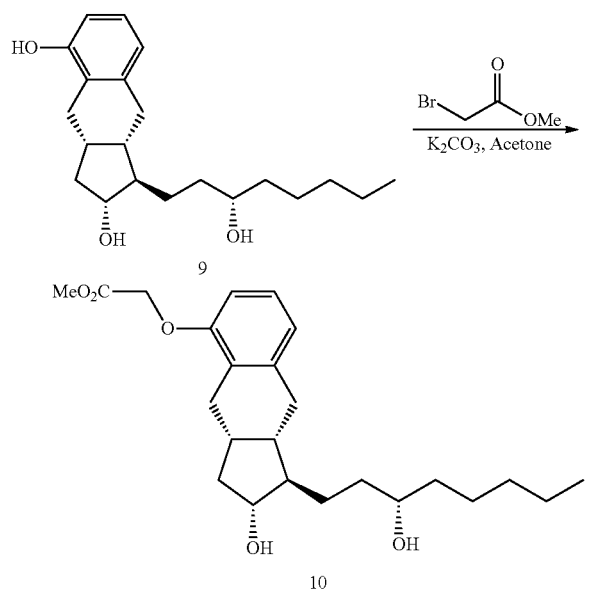

A mixture of 1.0 g of compound 9, 0.58 g of methyl bromoacetate, and 0.83 g of potassium carbonate ($K_2CO_3$) was dissolved in 15 mL of acetone. The reaction solution was heated and refluxed for 8 h. After the reaction solution was cooled to room temperature, the reaction solution was filtered to remove potassium carbonate. The filtrate was concentrated in vacuum and dried to yield 1.4 g of compound 10.

Example 13

Preparation of Compound 11 (Treprostinil)—Hydrolysis (i)

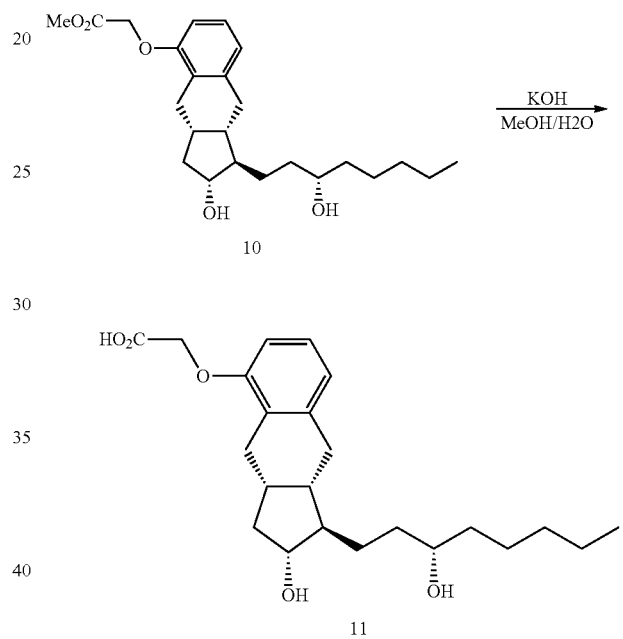

A mixture of 1.4 g of compound 10 and 0.34 g of potassium hydroxide (KOH) was dissolved in 10 mL of methanol and 10 mL of water. The reaction solution was next heated and refluxed for 2 h. After cooled to room temperature, 5.5 mL of aqueous 2N HCl was added, and the reaction solution was stirred for 2 hours. The reaction solution was then filtered and the resulting crude solid was washed using methanol and water (5 mL/10 mL). The solid was next dried under high vacuum to yield 1.2 g of compound 11 (Treprostinil). $^1$H NMR (MeOD, 400 MHz) δ 7.04 (t, J=7.9 Hz, 1H), 6.79 (d, J=7.3 Hz, 1H), 6.70 (d, J=8.2 Hz, 1H), 4.62 (s, 2H), 3.66-3.58 (m, 1H), 3.56-3.49 (m, 1H), 2.77 (dd, J=14.7, 6.2 Hz, 1H), 2.73 (dd, J=14.2, 6.2 Hz, 1H), 2.64 (dd, J=14.7, 6.0 Hz, 1H), 2.50 (dd, J=14.3, 6.0 Hz, 1H), 2.33-2.21 (m, 1H), 2.12-2.04 (m, 1H), 1.96-1.87 (m, 1H), 1.76-1.66 (m, 1H), 1.66-1.53 (m, 2H), 1.53-1.26 (m, 9H), 1.25-1.16 (m, 1H), 1.15-1.06 (m, 1H), 0.92 (t, J=6.8 Hz, 3H); $^{13}$C NMR (MeOD, 100 MHz) δ 173.1, 156.7, 142.3, 128.9, 127.3, 122.6, 111.0, 77.8, 73.1, 66.7, 52.6, 42.5, 42.2, 38.4, 36.2, 34.7, 34.2, 33.3, 29.8, 26.8, 26.6, 23.9, 14.6.

Example 14

Preparation of Compound 12 (treprostinil diethanolamine)—Salt Formation (j)

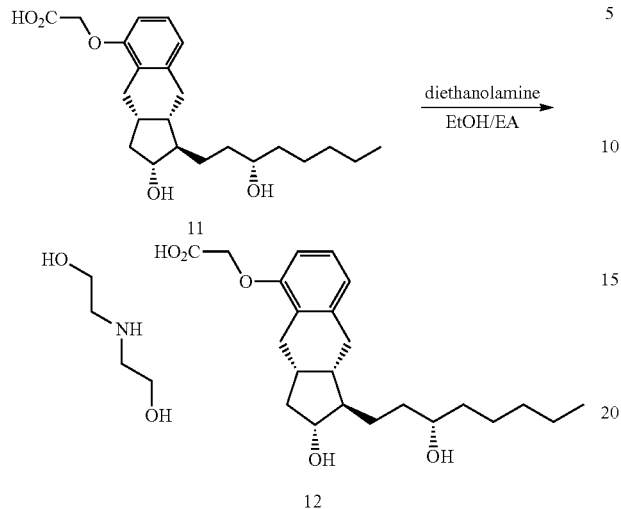

A mixture of 1.1 g of compound 11 (treprostinil) and 0.35 g of diethanolamine was dissolved in 4 mL of ethanol and 28 mL of ethyl acetate (EtOH/EA). The reaction solution was heated to 70° C. and stirred for 0.5 h. After the reaction solution was cooled to 55° C., 0.01 g of polymorph B of treprostinil diethanolamine as seed was added and the reaction solution was stirred for 1 h. The reaction solution was then cooled to room temperature and stirred for 16 h. After the reaction solution was filtered, the resulting solid was washed using 20 mL of ethyl acetate. The solid was then dried under high vacuum to yield 1.3 g of compound 12 (Treprostinil diethanolamine). $^1$H NMR (MeOD, 400 MHz) δ 7.01 (t, J=7.8 Hz, 1H), 6.74 (d, J=7.4 Hz, 1H), 6.70 (d, J=8.2 Hz, 1H), 4.34 (s, 2H), 3.78 (t, J=5.3 Hz, 4H), 3.66-3.58 (m, 1H), 3.56-3.49 (m, 1H), 3.11 (t, J=5.2 Hz, 4H), 2.83 (dd, J=14.7, 6.1 Hz, 1H), 2.73 (dd, J=14.2, 6.1 Hz, 1H), 2.62 (dd, J=14.7, 6.1 Hz, 1H), 2.48 (dd, J=14.1, 6.1 Hz, 1H), 2.31-2.22 (m, 1H), 2.14-2.05 (m, 1H), 1.94-1.84 (m, 1H), 1.77-1.67 (m, 1H), 1.67-1.52 (m, 2H), 1.52-1.39 (m, 4H), 1.39-1.26 (m, 5H), 1.26-1.18 (m, 1H), 1.18-1.07 (m, 1H), 0.92 (t, J=6.8 Hz, 3H); $^{13}$C NMR (MeOD, 100 MHz) δ 177.2, 157.2, 141.9, 128.6, 127.0, 121.7, 111.1, 77.7, 72.9, 69.3, 57.9, 52.8, 50.4, 42.4, 42.1, 38.3, 36.1, 34.8, 34.2, 33.1, 29.7, 26.8, 26.4, 23.7, 14.4.

It should be understood that these examples are merely illustrations of the present invention. The scope of the present invention should not be construed as those being defined above. Instead, the scope of the present invention shall be limited only by the appended claims.

What is claimed is:

1. A compound of formula (II):

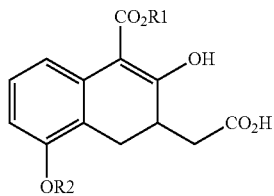

(II)

wherein each of R1 and R2 is a C1-6 alkyl group independently.

2. The compound as claimed in claim 1, wherein R1 is a methyl group.

3. The compound as claimed in claim 1, wherein R2 is a methyl group.

4. A method for preparing a compound of formula (IV):

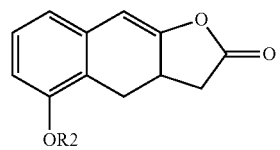

(IV)

wherein the method comprises the following steps:

(1) transforming a compound of formula (II) to obtain the compound of formula (IV);

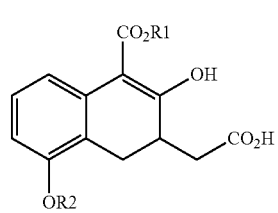

(II)

wherein each of R1 and R2 is a C1-6 alkyl group independently.

5. The method as claimed in claim 4, wherein step (1) comprises the following steps:

(1-1) performing a decarbomethoxylation reaction using the compound of formula (II) to obtain a compound of formula (III); and

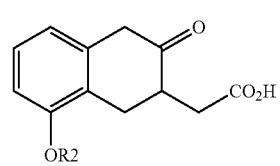

(III)

(1-2) performing a lactonization reaction using the compound of formula (III) to obtain a compound of formula (IV);

wherein R2 is a C1-6 alkyl group.

6. The method as claimed in claim 5, wherein R2 is a methyl group.

7. A method for preparing treprostinil diethanolamine represented by formula (XII):

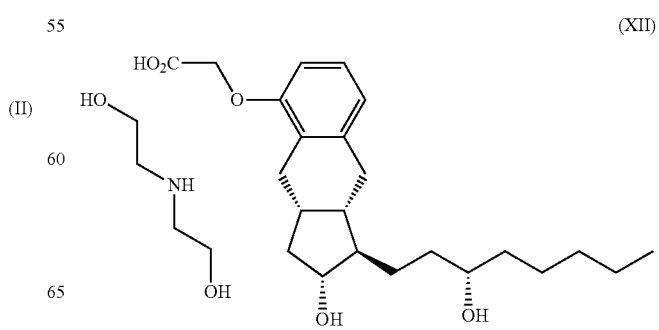

(XII)

wherein the method comprises the following steps:
(A) reacting a compound of formula (IV)

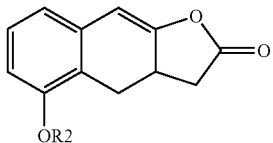
(IV)

with

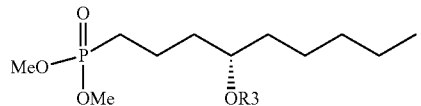

to perform a cyclization reaction to obtain a compound of formula (V):

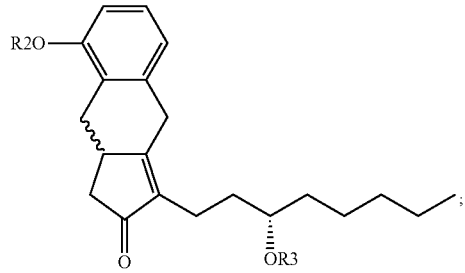
(V)

wherein R2 is a C1-6 alkyl group and R3 is a hydroxyl-protecting group;
(B) hydrogenating the compound of formula (V) to obtain a compound of formula (VI):

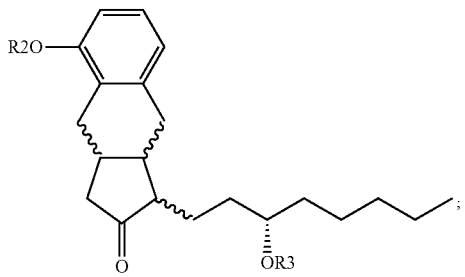
(VI)

(C) reducing the compound of formula (VI) to obtain a compound of formula (VII):

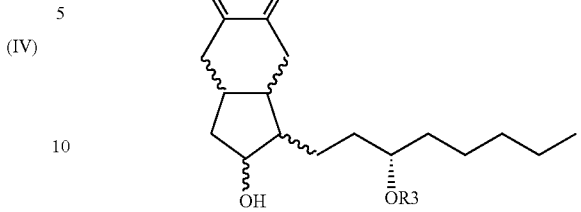
(VII)

(D) deprotecting the compound of formula (VII) to obtain a compound of formula (VIII):

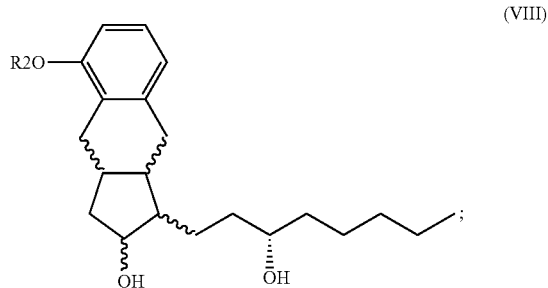
(VIII)

(E) performing a stereo-selective acetylation reaction using the compound of formula (VIII) in the presence of a lipase to obtain a compound of formula (VIII-1):

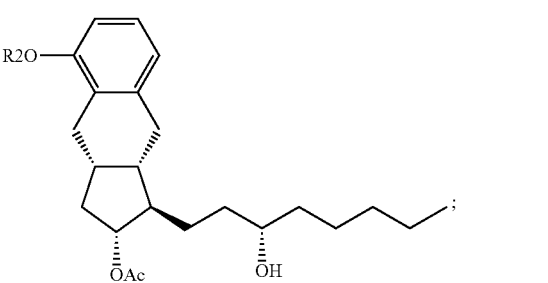
(VIII-1)

(F) performing a deacetylation reaction using the compound of formula (VIII-1) to obtain a compound of formula (VIII'):

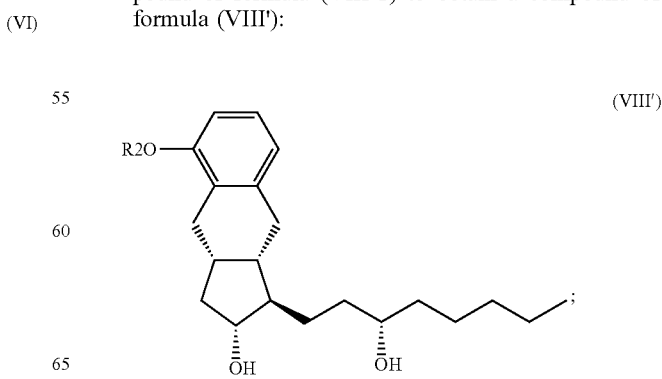
(VIII')

(G) performing a dealkylation reaction using the compound of formula (VIII') to obtain a compound of formula (IX):

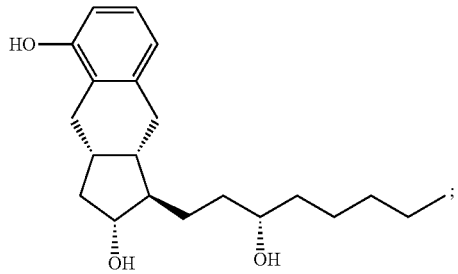
(IX)

(H) performing an alkylation reaction using the compound of formula (IX) by reacting with

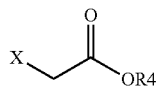

to obtain a compound of formula (X):

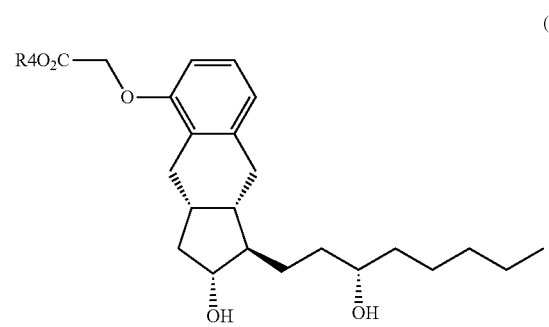
(X)

wherein R4 is a C1-5 alkyl group;

(I) hydrolyzing the compound of formula (X) to obtain a treprostinil represented by formula (XI):

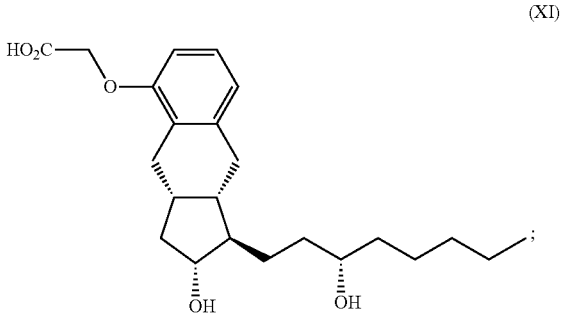 [SMILES: CCCCC[C@H](O)CC[C@@H]1[C@H]2Cc3cccc(OCC(=O)O)c3C[C@H]2C[C@H]1O]
(XI)

and (J) performing a salt formation reaction using the compound of formula (XI) to obtain a treprostinil diethanolamine represented by formula (XII).

8. The method as claimed in claim 7, wherein R2 is a methyl group.

9. The method as claimed in claim 7, wherein in step (A), the hydroxyl-protecting group is selected from the group consisting of methyl group, ethyl group, tert-butyl group, acetyl group, pivaloyl group (Piv), benzyl group (Bn), p-methoxy benzyl group (PMB), 9-fluorenylmethyl group (Fm), diphenylmethyl group (DPM), trimethylsilyl group (TMS), tert-butyldimethylsilyl group (TBS), triisopropylsilyl group (TIPS), 2-methoxylethoxymethyl group (MEM), methylthiomethy group (MTM), methoxymethyl group (MOM), and tetrahydropyranyl group (THP).

10. The method as claimed in claim 7, wherein in step (H), R4 is a methyl group.

11. A compound of formula (VIII-1):

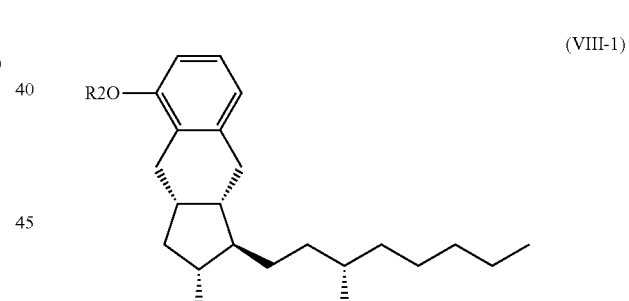
(VIII-1)

wherein R2 is a C1-6 alkyl group.

12. The compound as claimed in claim 11, wherein R2 is a methyl group.

* * * * *